US010052194B2

(12) United States Patent
Bumbalough

(10) Patent No.: US 10,052,194 B2
(45) Date of Patent: Aug. 21, 2018

(54) ACCOMMODATING INTRAOCULAR LENSES

(75) Inventor: Timothy R. Bumbalough, Fullerton, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 288 days.

(21) Appl. No.: 12/822,906

(22) Filed: Jun. 24, 2010

(65) Prior Publication Data

US 2011/0054600 A1   Mar. 3, 2011

Related U.S. Application Data

(60) Provisional application No. 61/220,887, filed on Jun. 26, 2009.

(51) Int. Cl.
*A61F 2/16* (2006.01)

(52) U.S. Cl.
CPC .......... *A61F 2/1613* (2013.01); *A61F 2/1624* (2013.01); *A61F 2/1635* (2013.01); *A61F 2/1694* (2013.01); *A61F 2/1648* (2013.01); *A61F 2002/1681* (2013.01); *A61F 2002/16901* (2015.04)

(58) Field of Classification Search
CPC ........ A61F 2/16; A61F 2/1613; A61F 2/1616; A61F 2/1618; A61F 2/1624; A61F 2/1635; A61F 2002/1681; A61F 2002/1682; A61F 2002/169; A61F 2002/16901
USPC .............................. 623/6.37–6.41, 6.43, 6.46
See application file for complete search history.

(56) References Cited

U.S. PATENT DOCUMENTS

| 1,483,509 A | 2/1924 | Bugbee |
| 2,129,305 A | 9/1938 | William |
| 2,274,142 A | 2/1942 | Houchin |
| 2,405,989 A | 8/1946 | Beach |
| 2,511,517 A | 6/1950 | Spiegel |
| 2,834,023 A | 5/1958 | Lieb |
| 3,004,470 A | 10/1961 | Hans |
| 3,031,927 A | 5/1962 | Wesley |
| 3,034,403 A | 5/1962 | Neefe |
| RE25,286 E | 11/1962 | De Carle |

(Continued)

FOREIGN PATENT DOCUMENTS

| AU | 3225789 A1 | 10/1989 |
| CA | 2752743 A1 | 9/2010 |

(Continued)

OTHER PUBLICATIONS

English translation of WO 93/05733 A1.

(Continued)

*Primary Examiner* — Leslie Lopez
(74) *Attorney, Agent, or Firm* — Johnson & Johnson Surgical Vision, Inc.

(57) ABSTRACT

An intraocular lens is disclosed, with an optic that changes shape in response to a deforming force exerted by the zonules of the eye. A haptic supports the optic around its equator and couples the optic to the capsular bag of the eye. Certain haptic features improve the accommodative performance of the haptic, such that compressive/tensile forces may be more efficiently transferred from the haptic to optic. Furthermore, certain aspects also provide enhanced bag-sizing capability so that the IOL better fits within the capsular bag.

18 Claims, 7 Drawing Sheets

(56) References Cited

U.S. PATENT DOCUMENTS

| | | |
|---|---|---|
| 3,210,894 A | 10/1965 | Bentley et al. |
| 3,222,432 A | 12/1965 | Grandperret |
| 3,227,507 A | 1/1966 | William |
| 3,305,294 A | 2/1967 | Alvarez |
| 3,339,997 A | 9/1967 | Wesley |
| 3,415,597 A | 12/1968 | Willard |
| 3,420,006 A | 1/1969 | Howard |
| 3,431,327 A | 3/1969 | George |
| 3,482,906 A | 12/1969 | David |
| 3,507,565 A | 4/1970 | Luis et al. |
| 3,542,461 A | 11/1970 | Louis et al. |
| 3,583,790 A | 6/1971 | Baker |
| 3,617,116 A | 11/1971 | Jones |
| 3,632,696 A | 1/1972 | Donald |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,326,306 A | 4/1982 | Poler |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A * | 4/1984 | Hessburg ............... 623/6.51 |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright et al. |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |
| 4,650,292 A | 3/1987 | Baker et al. |
| 4,655,770 A | 4/1987 | Gupta et al. |
| 4,661,108 A | 4/1987 | Grendahl et al. |
| 4,662,882 A | 5/1987 | Hoffer |
| 4,664,666 A | 5/1987 | Barrett |
| 4,666,444 A | 5/1987 | Pannu |
| 4,666,445 A | 5/1987 | Tillay |
| 4,676,792 A | 6/1987 | Praeger |
| 4,676,793 A | 6/1987 | Bechert, II |
| 4,687,484 A | 8/1987 | Kaplan |
| 4,693,572 A | 9/1987 | Tsuetaki et al. |
| 4,693,716 A | 9/1987 | MacKool |
| RE32,525 E | 10/1987 | Pannu |
| 4,702,244 A | 10/1987 | Mazzocco |
| 4,704,016 A | 11/1987 | De Carle |
| 4,710,193 A | 12/1987 | Volk |
| 4,710,194 A | 12/1987 | Kelman |
| 4,711,638 A | 12/1987 | Lindstrom |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,780,154 A | 10/1988 | Mori et al. |
| 4,781,718 A | 11/1988 | Lindstrom |
| 4,787,903 A | 11/1988 | Grendahl |
| 4,790,847 A | 12/1988 | Woods |

(56) References Cited

U.S. PATENT DOCUMENTS

| | | |
|---|---|---|
| 4,808,170 A | 2/1989 | Thornton et al. |
| 4,813,955 A | 3/1989 | Achatz et al. |
| 4,816,030 A | 3/1989 | Robinson |
| 4,816,031 A | 3/1989 | Pfoff |
| 4,816,032 A | 3/1989 | Hetland |
| 4,822,360 A | 4/1989 | Deacon |
| 4,828,558 A | 5/1989 | Kelman |
| 4,830,481 A | 5/1989 | Futhey et al. |
| 4,834,749 A | 5/1989 | Orlosky |
| 4,840,627 A | 6/1989 | Blumenthal |
| 4,842,601 A | 6/1989 | Smith |
| 4,863,463 A | 9/1989 | Tjan |
| 4,865,601 A | 9/1989 | Caldwell et al. |
| 4,878,910 A | 11/1989 | Koziol et al. |
| 4,878,911 A | 11/1989 | Anis |
| 4,880,427 A | 11/1989 | Anis |
| 4,881,804 A | 11/1989 | Cohen |
| 4,883,485 A | 11/1989 | Patel |
| 4,888,012 A | 12/1989 | Horn et al. |
| 4,888,014 A | 12/1989 | Nguyen |
| 4,888,015 A | 12/1989 | Domino |
| 4,888,016 A | 12/1989 | Langerman |
| 4,890,912 A | 1/1990 | Visser |
| 4,890,913 A | 1/1990 | De Carle |
| 4,892,543 A | 1/1990 | Turley |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,080 A | 2/1991 | Shepard |
| 4,994,082 A | 2/1991 | Richards et al. |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wiley et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk |
| 5,180,390 A | 1/1993 | Drews |
| 5,192,317 A | 3/1993 | Kalb |
| 5,192,318 A | 3/1993 | Schneider et al. |
| 5,196,026 A | 3/1993 | Barrett et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barrett et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A | 12/1994 | Christ et al. |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,988 E | 7/1995 | Yang |
| RE34,998 E | 7/1995 | Langerman |
| 5,443,506 A * | 8/1995 | Garabet ............... A61F 2/1627 351/159.04 |
| 5,476,445 A | 12/1995 | Baerveldt et al. |
| 5,476,514 A | 12/1995 | Cumming |
| 5,480,428 A | 1/1996 | Fedorov et al. |
| 5,489,301 A | 2/1996 | Barber |
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,523,029 A | 6/1996 | Korgel et al. |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |

(56) References Cited

U.S. PATENT DOCUMENTS

| | | |
|---|---|---|
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |
| 5,766,244 A | 6/1998 | Binder |
| 5,769,890 A | 6/1998 | McDonald |
| 5,770,125 A | 6/1998 | O'Connor et al. |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,864,378 A | 1/1999 | Portney |
| 5,869,549 A | 2/1999 | Christ et al. |
| RE36,150 E | 3/1999 | Gupta |
| 5,876,441 A | 3/1999 | Shibuya |
| 5,876,442 A | 3/1999 | Lipshitz et al. |
| 5,885,279 A | 3/1999 | Bretton |
| 5,895,422 A | 4/1999 | Hauber |
| 5,898,473 A | 4/1999 | Seidner et al. |
| 5,928,283 A | 7/1999 | Gross et al. |
| 5,929,969 A | 7/1999 | Roffman |
| 5,968,094 A | 10/1999 | Werblin et al. |
| 5,984,962 A | 11/1999 | Anello et al. |
| 6,013,101 A | 1/2000 | Israel |
| 6,015,435 A | 1/2000 | Valunin et al. |
| 6,050,970 A | 4/2000 | Baerveldt |
| 6,051,024 A | 4/2000 | Cumming |
| 6,063,118 A | 5/2000 | Nagamoto |
| 6,083,261 A | 7/2000 | Callahan et al. |
| 6,090,141 A | 7/2000 | Lindstrom |
| 6,096,078 A | 8/2000 | McDonald |
| 6,102,946 A | 8/2000 | Nigam |
| 6,106,553 A | 8/2000 | Feingold |
| 6,106,554 A | 8/2000 | Bretton |
| 6,110,202 A | 8/2000 | Barraquer et al. |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,139,576 A | 10/2000 | Doyle et al. |
| 6,152,958 A | 11/2000 | Nordan |
| 6,162,249 A | 12/2000 | Deacon et al. |
| 6,176,878 B1 | 1/2001 | Gwon et al. |
| 6,186,148 B1 | 2/2001 | Okada |
| 6,197,058 B1 | 3/2001 | Portney |
| 6,197,059 B1 | 3/2001 | Cumming |
| 6,200,342 B1 | 3/2001 | Tassignon |
| 6,210,005 B1 | 4/2001 | Portney |
| 6,217,612 B1 | 4/2001 | Woods |
| 6,221,105 B1 | 4/2001 | Portney |
| 6,224,628 B1 | 5/2001 | Callahan et al. |
| 6,228,115 B1 | 5/2001 | Hoffmann et al. |
| 6,231,603 B1 | 5/2001 | Lang et al. |
| 6,238,433 B1 | 5/2001 | Portney |
| 6,241,777 B1 | 6/2001 | Kellan |
| 6,251,312 B1 | 6/2001 | Phan et al. |
| 6,258,123 B1 | 7/2001 | Young et al. |
| 6,261,321 B1 | 7/2001 | Kellan |
| 6,277,146 B1 | 8/2001 | Peyman et al. |
| 6,277,147 B1 | 8/2001 | Christ et al. |
| 6,280,471 B1 | 8/2001 | Peyman et al. |
| 6,299,641 B1 | 10/2001 | Woods |
| 6,302,911 B1 | 10/2001 | Hanna |
| 6,322,213 B1 | 11/2001 | Altieri et al. |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,364,906 B1 | 4/2002 | Baikoff et al. |
| 6,387,126 B1 | 5/2002 | Cumming |
| 6,399,734 B1 | 6/2002 | Hodd et al. |
| 6,406,494 B1 | 6/2002 | Laguette et al. |
| 6,423,094 B1 | 7/2002 | Sarfarazi |
| 6,425,917 B1 | 7/2002 | Blake |
| 6,443,985 B1 * | 9/2002 | Woods ............... 623/6.46 |
| 6,450,642 B1 | 9/2002 | Jethmalani et al. |
| 6,454,802 B1 | 9/2002 | Bretton et al. |
| 6,457,826 B1 | 10/2002 | Lett |
| 6,464,725 B2 | 10/2002 | Skotton et al. |
| 6,468,306 B1 | 10/2002 | Paul et al. |
| 6,474,814 B1 | 11/2002 | Griffin |
| 6,475,240 B1 | 11/2002 | Paul |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,533,813 B1 | 3/2003 | Lin et al. |
| 6,533,814 B1 | 3/2003 | Jansen |
| 6,536,899 B1 | 3/2003 | Fiala |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,589,550 B1 | 7/2003 | Hodd et al. |
| 6,592,621 B1 | 7/2003 | Domino |
| 6,598,606 B2 | 7/2003 | Terwee et al. |
| 6,599,317 B1 | 7/2003 | Weinschenk, III |
| 6,609,793 B2 | 8/2003 | Norrby et al. |
| 6,616,691 B1 | 9/2003 | Tran |
| 6,616,692 B1 | 9/2003 | Glick et al. |
| 6,616,693 B1 | 9/2003 | Nguyen |
| 6,638,305 B2 | 10/2003 | Laguette |
| 6,638,306 B2 | 10/2003 | Cumming |
| 6,645,246 B1 | 11/2003 | Weinschenk, III |
| 6,660,035 B1 | 12/2003 | Lang et al. |
| 6,685,315 B1 | 2/2004 | De |
| 6,695,881 B2 | 2/2004 | Peng et al. |
| 6,721,104 B2 | 4/2004 | Schachar et al. |
| 6,730,123 B1 | 5/2004 | Klopotek |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,017 B1 | 11/2004 | Shu |
| 6,818,158 B2 | 11/2004 | Pham et al. |
| 6,827,738 B2 * | 12/2004 | Willis et al. ............... 623/6.43 |
| 6,836,374 B2 | 12/2004 | Esch et al. |
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,884,262 B2 | 4/2005 | Brady et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 6,930,838 B2 | 8/2005 | Schachar |
| 6,932,839 B1 | 8/2005 | Kamerling et al. |
| 6,942,695 B1 | 9/2005 | Chapoy et al. |
| 6,966,649 B2 | 11/2005 | Shadduck |
| 7,018,409 B2 | 3/2006 | Glick et al. |
| 7,021,760 B2 | 4/2006 | Newman |
| 7,025,783 B2 | 4/2006 | Brady et al. |
| 7,041,134 B2 | 5/2006 | Nguyen et al. |
| 7,073,906 B1 | 7/2006 | Portney |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |

(56) References Cited

U.S. PATENT DOCUMENTS

| | | |
|---|---|---|
| 7,125,422 B2 | 10/2006 | Woods et al. |
| 7,150,759 B2 | 12/2006 | Paul et al. |
| 7,179,292 B2 | 2/2007 | Worst et al. |
| 7,182,780 B2 | 2/2007 | Terwee et al. |
| 7,186,266 B2 | 3/2007 | Peyman |
| 7,188,949 B2 | 3/2007 | Bandhauer et al. |
| 7,198,640 B2 | 4/2007 | Nguyen |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,247,168 B2 | 7/2007 | Esch et al. |
| 7,261,737 B2 | 8/2007 | Esch et al. |
| 7,344,617 B2 | 3/2008 | Dubrow |
| 7,452,362 B2 | 11/2008 | Zadno-Azizi et al. |
| 7,452,378 B2 | 11/2008 | Zadno-Azizi et al. |
| 7,503,938 B2 | 3/2009 | Phillips |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 7,922,326 B2 | 4/2011 | Bandhauer et al. |
| 8,034,108 B2 | 10/2011 | Bumbalough |
| 8,052,752 B2 | 11/2011 | Woods et al. |
| 8,343,217 B2 | 1/2013 | Bumbalough |
| 9,198,752 B2 | 12/2015 | Woods |
| 9,277,987 B2 | 3/2016 | Smiley et al. |
| 9,364,318 B2 | 6/2016 | Beer |
| 9,433,498 B2 | 9/2016 | Masket et al. |
| 2001/0001836 A1 | 5/2001 | Cumming |
| 2001/0004708 A1 | 6/2001 | Nagai |
| 2001/0018612 A1 | 8/2001 | Carson et al. |
| 2001/0039451 A1 | 11/2001 | Barnett |
| 2001/0044657 A1 | 11/2001 | Kellan |
| 2002/0004682 A1 | 1/2002 | Zhou et al. |
| 2002/0011167 A1 | 1/2002 | Figov et al. |
| 2002/0072796 A1 | 6/2002 | Hoffmann et al. |
| 2002/0103536 A1 | 8/2002 | Landreville et al. |
| 2002/0120329 A1 | 8/2002 | Lang et al. |
| 2002/0151973 A1 | 10/2002 | Arita et al. |
| 2002/0161434 A1 | 10/2002 | Laguette et al. |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0020425 A1 | 1/2003 | Ricotti |
| 2003/0033013 A1 | 2/2003 | Callahan et al. |
| 2003/0045933 A1 | 3/2003 | Brady |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0105522 A1 | 6/2003 | Glazier |
| 2003/0109925 A1 | 6/2003 | Ghazizadeh et al. |
| 2003/0114927 A1 | 6/2003 | Nagamoto |
| 2003/0130732 A1 | 7/2003 | Sarfarazi |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015236 A1 | 1/2004 | Sarfarazi |
| 2004/0034415 A1 | 2/2004 | Terwee et al. |
| 2004/0039446 A1 | 2/2004 | McNicholas |
| 2004/0082993 A1 | 4/2004 | Woods |
| 2004/0082995 A1 | 4/2004 | Woods |
| 2004/0106992 A1 | 6/2004 | Lang et al. |
| 2004/0111153 A1 | 6/2004 | Woods et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Messner et al. |
| 2004/0230299 A1 | 11/2004 | Simpson et al. |
| 2004/0230300 A1 | 11/2004 | Bandhauer et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 | 1/2005 | Shadduck |
| 2005/0021140 A1 | 1/2005 | Liao |
| 2005/0027354 A1 | 2/2005 | Brady et al. |
| 2005/0038510 A1 | 2/2005 | Portney et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0125056 A1 | 6/2005 | Deacon et al. |
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |
| 2005/0137703 A1 | 6/2005 | Chen |
| 2005/0234547 A1 | 10/2005 | Nguyen et al. |
| 2005/0246019 A1 | 11/2005 | Blake et al. |
| 2005/0267575 A1 | 12/2005 | Nguyen et al. |
| 2005/0288785 A1 | 12/2005 | Portney et al. |
| 2006/0030938 A1 | 2/2006 | Altmann |
| 2006/0064162 A1 | 3/2006 | Klima |
| 2006/0095127 A1 | 5/2006 | Feingold et al. |
| 2006/0098162 A1 | 5/2006 | Bandhauer et al. |
| 2006/0100703 A1 | 5/2006 | Evans et al. |
| 2006/0111776 A1 | 5/2006 | Glick et al. |
| 2006/0116764 A1 | 6/2006 | Simpson |
| 2006/0116765 A1 | 6/2006 | Blake et al. |
| 2006/0149369 A1 | 7/2006 | Cumming et al. |
| 2006/0178741 A1 | 8/2006 | Zadno-Azizi et al. |
| 2006/0184244 A1 | 8/2006 | Nguyen et al. |
| 2006/0209430 A1 | 9/2006 | Spivey |
| 2006/0209431 A1 | 9/2006 | Spivey |
| 2006/0235513 A1 | 10/2006 | Price, Jr. |
| 2006/0238702 A1 | 10/2006 | Glick et al. |
| 2006/0259139 A1 | 11/2006 | Zadno-Azizi et al. |
| 2006/0271187 A1 | 11/2006 | Zadno-Azizi et al. |
| 2007/0032866 A1 | 2/2007 | Portney |
| 2007/0050025 A1 | 3/2007 | Nguyen et al. |
| 2007/0067872 A1 | 3/2007 | Mittendorf et al. |
| 2007/0078515 A1 | 4/2007 | Brady |
| 2007/0088433 A1 | 4/2007 | Esch et al. |
| 2007/0100444 A1 | 5/2007 | Brady et al. |
| 2007/0100445 A1* | 5/2007 | Shadduck ............... 623/6.37 |
| 2007/0106376 A1 | 5/2007 | Smith et al. |
| 2007/0106379 A1 | 5/2007 | Messner |
| 2007/0106381 A1 | 5/2007 | Blake |
| 2007/0108643 A1 | 5/2007 | Zadno-Azizi et al. |
| 2007/0123591 A1 | 5/2007 | Kuppuswamy et al. |
| 2007/0129798 A1 | 6/2007 | Chawdhary |
| 2007/0135915 A1* | 6/2007 | Klima ............... 623/6.37 |
| 2007/0156236 A1 | 7/2007 | Stenger |
| 2007/0213817 A1 | 9/2007 | Esch et al. |
| 2007/0258143 A1 | 11/2007 | Portney |
| 2007/0260309 A1 | 11/2007 | Richardson |
| 2007/0282247 A1 | 12/2007 | Desai et al. |
| 2007/0299487 A1 | 12/2007 | Shadduck |
| 2008/0004699 A1 | 1/2008 | Ben Nun |
| 2008/0125790 A1 | 5/2008 | Tsai et al. |
| 2008/0140192 A1 | 6/2008 | Humayun et al. |
| 2008/0161913 A1* | 7/2008 | Brady ............... A61F 2/1635 623/6.43 |
| 2008/0161914 A1* | 7/2008 | Brady ............... A61F 2/1635 623/6.46 |
| 2008/0300680 A1 | 12/2008 | Joshua |
| 2009/0012609 A1 | 1/2009 | Geraghty et al. |
| 2009/0234448 A1 | 9/2009 | Weeber et al. |

(56) References Cited

U.S. PATENT DOCUMENTS

| | | |
|---|---|---|
| 2009/0248154 A1 | 10/2009 | Dell |
| 2010/0057203 A1 | 3/2010 | Glick et al. |
| 2010/0228346 A1 | 9/2010 | Esch |
| 2011/0035001 A1 | 2/2011 | Woods |
| 2011/0251686 A1 | 10/2011 | Masket |
| 2012/0046744 A1 | 2/2012 | Woods et al. |
| 2015/0173890 A1 | 6/2015 | Portney et al. |
| 2016/0220351 A1 | 8/2016 | Dorronsoro et al. |

FOREIGN PATENT DOCUMENTS

| | | |
|---|---|---|
| CH | 681687 A5 | 5/1993 |
| DE | 2702117 A1 | 7/1978 |
| DE | 3246306 A1 | 6/1984 |
| DE | 4038088 A1 | 6/1992 |
| DE | 19501444 A1 | 7/1996 |
| DE | 20109306 U1 | 8/2001 |
| DE | 10059482 A1 | 6/2002 |
| DE | 10125829 A1 | 11/2002 |
| EP | 64812 A2 | 11/1982 |
| EP | 162573 A2 | 11/1985 |
| EP | 212616 A2 | 3/1987 |
| EP | 246216 A2 | 11/1987 |
| EP | 328117 A2 | 8/1989 |
| EP | 329981 A1 | 8/1989 |
| EP | 331457 A2 | 9/1989 |
| EP | 336877 A1 | 10/1989 |
| EP | 0337390 A2 | 10/1989 |
| EP | 342895 A2 | 11/1989 |
| EP | 351471 A2 | 1/1990 |
| EP | 356050 A1 | 2/1990 |
| EP | 337390 A3 | 5/1990 |
| EP | 402825 A1 | 12/1990 |
| EP | 420549 A2 | 4/1991 |
| EP | 470811 A2 | 2/1992 |
| EP | 480748 A1 | 4/1992 |
| EP | 488835 A1 | 6/1992 |
| EP | 492126 A2 | 7/1992 |
| EP | 507292 A1 | 10/1992 |
| EP | 566170 A1 | 10/1993 |
| EP | 601845 A1 | 6/1994 |
| EP | 605841 A1 | 7/1994 |
| EP | 691109 A1 | 1/1996 |
| EP | 766540 A1 | 4/1997 |
| EP | 779063 A1 | 6/1997 |
| EP | 780718 A1 | 6/1997 |
| EP | 897702 A2 | 2/1999 |
| EP | 766540 B1 | 8/1999 |
| EP | 1108402 A2 | 6/2001 |
| EP | 1321112 A1 | 6/2003 |
| EP | 1647241 A2 | 4/2006 |
| EP | 1424049 B1 | 6/2009 |
| EP | 2523632 A2 | 11/2012 |
| FR | 488835 A | 11/1918 |
| FR | 2666504 A1 | 3/1992 |
| FR | 2666735 A1 | 3/1992 |
| FR | 2681524 A1 | 3/1993 |
| FR | 2745711 A1 | 9/1997 |
| FR | 2778093 A1 | 11/1999 |
| FR | 2784575 A1 | 4/2000 |
| GB | 939016 A | 10/1963 |
| GB | 2058391 A | 4/1981 |
| GB | 2124500 A | 2/1984 |
| GB | 2129155 A | 5/1984 |
| GB | 2146791 A | 4/1985 |
| GB | 2192291 A | 1/1988 |
| GB | 2215076 A | 9/1989 |
| JP | 0211134 | 1/1990 |
| JP | 2126847 | 5/1990 |
| JP | H06508279 | 9/1994 |
| JP | 7005399 A2 | 1/1995 |
| JP | 7222760 A2 | 8/1995 |
| JP | H09501856 A | 2/1997 |
| JP | H09502542 A | 3/1997 |
| JP | 10000211 A2 | 1/1998 |
| JP | H11500030 A | 1/1999 |
| JP | 11047168 A2 | 2/1999 |
| JP | 2000508588 T2 | 7/2000 |
| JP | 2003513704 T | 4/2003 |
| JP | 2003190193 A | 7/2003 |
| JP | 2003522592 T2 | 7/2003 |
| JP | 2003525694 A | 9/2003 |
| RU | 2014038 C1 | 6/1994 |
| RU | 2014039 C1 | 6/1994 |
| WO | 8404449 A1 | 11/1984 |
| WO | 8603961 A1 | 7/1986 |
| WO | 8700299 A1 | 1/1987 |
| WO | 8707496 A1 | 12/1987 |
| WO | 8803961 A1 | 6/1988 |
| WO | 8902251 A1 | 3/1989 |
| WO | 8911672 A1 | 11/1989 |
| WO | 8911872 A1 | 12/1989 |
| WO | 9000889 A1 | 2/1990 |
| WO | 9109336 A1 | 6/1991 |
| WO | 9302639 A1 | 2/1993 |
| WO | 9416648 A1 | 8/1994 |
| WO | 9503783 A1 | 2/1995 |
| WO | 9610968 A1 | 4/1996 |
| WO | 9615734 A2 | 5/1996 |
| WO | 9625126 A1 | 8/1996 |
| WO | 9635398 A1 | 11/1996 |
| WO | 9712272 A1 | 4/1997 |
| WO | 9727825 A1 | 8/1997 |
| WO | 9743984 A1 | 11/1997 |
| WO | 9805273 A1 | 2/1998 |
| WO | 9821621 A1 | 5/1998 |
| WO | 9849594 A1 | 11/1998 |
| WO | 9856315 A1 | 12/1998 |
| WO | 9903427 A1 | 1/1999 |
| WO | 9907309 A1 | 2/1999 |
| WO | 9920206 A1 | 4/1999 |
| WO | 9921491 A1 | 5/1999 |
| WO | 9929266 A1 | 6/1999 |
| WO | 0021467 A1 | 4/2000 |
| WO | 0027315 A1 | 5/2000 |
| WO | 0035379 A1 | 6/2000 |
| WO | 0046629 A1 | 8/2000 |
| WO | 0059407 A1 | 10/2000 |
| WO | 0061036 A1 | 10/2000 |
| WO | 0066037 A1 | 11/2000 |
| WO | 0066039 A1 | 11/2000 |
| WO | 0066040 A1 | 11/2000 |
| WO | 0066041 A1 | 11/2000 |
| WO | 0108605 A1 | 2/2001 |
| WO | 0119289 A1 | 3/2001 |
| WO | WO0119288 A1 | 3/2001 |
| WO | 0128144 A1 | 4/2001 |
| WO | 0134061 A1 | 5/2001 |
| WO | 0134066 A1 | 5/2001 |
| WO | 0134067 A1 | 5/2001 |
| WO | 0156510 A1 | 8/2001 |
| WO | 0160286 A1 | 8/2001 |
| WO | 0164135 A1 | 9/2001 |
| WO | 0164136 A2 | 9/2001 |
| WO | 0166042 A1 | 9/2001 |
| WO | 0182839 A1 | 11/2001 |
| WO | 0189816 A1 | 11/2001 |
| WO | 0209620 A1 | 2/2002 |
| WO | 0212523 | 2/2002 |
| WO | WO0219949 A2 | 3/2002 |
| WO | 02058391 A2 | 7/2002 |
| WO | 02071983 A1 | 9/2002 |
| WO | 02098328 A1 | 12/2002 |
| WO | 03009051 A2 | 1/2003 |
| WO | 03015657 A2 | 2/2003 |
| WO | 03015669 A1 | 2/2003 |
| WO | 03034949 A2 | 5/2003 |
| WO | 03049646 A2 | 6/2003 |
| WO | 03057081 A2 | 7/2003 |
| WO | 03059196 A2 | 7/2003 |
| WO | 03059208 A2 | 7/2003 |
| WO | 03075810 A1 | 9/2003 |
| WO | 03084441 A1 | 10/2003 |
| WO | 03092552 A1 | 11/2003 |

(56) References Cited

FOREIGN PATENT DOCUMENTS

| | | |
|---|---|---|
| WO | 04000171 A1 | 12/2003 |
| WO | 04020549 A1 | 3/2004 |
| WO | 04037127 A2 | 5/2004 |
| WO | 04073559 A1 | 9/2004 |
| WO | 05011531 A2 | 2/2005 |
| WO | 05018504 A1 | 3/2005 |
| WO | 2005019871 A2 | 3/2005 |
| WO | 03082147 A3 | 8/2005 |
| WO | 05084587 A2 | 9/2005 |
| WO | WO2005115278 A1 | 12/2005 |
| WO | 06025726 A1 | 3/2006 |
| WO | 06118452 A1 | 11/2006 |
| WO | 2007040964 A1 | 4/2007 |
| WO | 2007067872 A2 | 6/2007 |
| WO | WO2008079671 A1 | 7/2008 |
| WO | WO20080777925 A2 | 7/2008 |
| WO | WO 2008/108524 A1 * | 9/2008 .............. A61F 2/14 |
| WO | WO2009021327 A1 | 2/2009 |
| WO | 2010093823 A2 | 8/2010 |
| WO | 2011017322 A1 | 2/2011 |
| ZA | 8808414 A | 7/1989 |

OTHER PUBLICATIONS

U.S. Appl. No. 09/656,661, filed Sep. 7, 2000.
Thornton S., "Accommodation in Pseudophakia," 1991, pp. 159-162.
U.S. Appl. No. 09/721,072, filed Nov. 22, 2000.
International Search Report for Application No. PCT/US2010/039860, dated Dec. 14, 2010, 4 pages.
Partial International Search Report for Application No. PCT/US2010/039858, dated Oct. 5, 2010, 2 pages.
International Search Report for Application No. PCT/US2010/039858, dated Jan. 20, 2011, 3 pages.
World Optics Inc., Ophthalmology Times, Mar. 15, 1995.
Adler-Grinberg D., "Questioning Our Classical Understanding of Accomodation and Presbyopia," American Journal of Optometry & Physiological Optics, 1986, vol. 63 (7), pp. 571-580.
Altan-Yaycioglu R., et al., "Pseudo-accomodation with Intraocular Lenses Implanted in the Bag," Journal of Refractive Surgery, 2002, vol. 18 (3), pp. 271-275.
Amo Specs Model AC-21B, AMO Classic Series, 1992, 1 page.
Chauvin-Opsia, Azurite ACL (0459).
Chiron, Clemente Optfit Model SP525, Brochure Translation, Jul. 12, 1998.
Chrion Vision, Nuvita MA20, 1997, 1 page.
Cohen A.L., "Diffractive Bifocal Lens Design," Optometry and Vision Science, 1993, vol. 70 (6), pp. 461-468.
Cohen A.L., "Practical Design of a Bifocal Hologram Contact Lens or Intraocular Lens," Applied Optics, 1992, vol. 31 (19), pp. 3750-3754.
European Search Report for Application No. EP09009432, dated Aug. 27, 2009, 2 pages.
European Search Report for Application No. EP09178394, dated Jan. 25, 2010, 2 pages.
European Search Report for Application No. EP10181797, dated Jan. 28, 2011, 2 pages.
European Search Report for Application No. EP11152227, dated Oct. 21, 2011, 7 pages.
Extended European Search Report for Application No. EP11152508, dated Oct. 25, 2011, 7 pages.
Fechner P.U., et al., "Iris-Claw Lens in Phakic Eyes to Correct Hyperopia: Preliminary Study," Journal of Cataract and Refractive Surgery, 1998, vol. 24 (1), pp. 48-56.
Foldable Intraocular Lens Implants and Small Incision Cataract Surgery, Ohio Valley Eye Physicians, 2004.
Hanita Lenses, Source Ocular Surgery News International, 1 page.
Hara T., et al., "Accommodative Intraocular Lens with Spring Action Part 1 Design and Placement in an Excised Animal Eye," Ophthalmic Surgery, 1990, vol. 21 (2), pp. 128-133.

Hecht E., et al., "Optics", 4th Edition, Addison-Wesley Publishing Company, 1979, pp. 188-190.
Holladay J.T., et al., "A Three-Part System for Refining Intraocular Lens Power Calculations," Journal of Cataract and Refractive Surgery, 1988, vol. 14 (1), pp. 17-24.
Holladay J.T., et al., "Analysis of Edge Glare Phenomena in Intraocular Lens Edge Designs," Journal of Cataract and Refractive Surgery, 1999, vol. 25 (6), pp. 748-752.
Iolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, 1999, vol. 117 (1), pp. 17-23.
Klien S.A., "Understanding the Diffractive Bifocal Contact Lens," Optometry and Vision Science, 1993, vol. 70 (6), pp. 439-460.
Kuchle M., et al., "Implantation of a New Accommodative Posterior Chamber Intraocular Lens," Journal of Refractive Surgery, 2002, vol. 18 (3), pp. 208-216.
Lane S.S., et al., "Polysulfone Intracorneal Lenses," International Ophthalmology Clinics, 1991, vol. 31 (1), pp. 37-46.
Mandell R.B., "Contact Lens Practice", 4th Edition, Charles C. Thomas Publishers, 1988, 11 pages.
Mandell R.B., et al., "Mathematical Model of the Corneal Contour," 1965, School of Optometry, University of California, Berkeley, pp. 183-197.
Marron J.C., et al., "Higher-order Kinoforms," Computer and Optically Formed Holographic Optics, 1990, vol. 1211, pp. 62-66.
McCarey B.E., et al., "Modeling Glucose Distribution In the Cornea," Current Eye Research, 1990, vol. 9 (11), pp. 1025-1039.
Mediphacos Ltda, Ocular Surgery News International.
Menezo J.L., et al., "Endothelial Study of Iris-Claw Phakic Lens: Four Year Follow-Up," Journal of Cataract Refractive Surgery, 1998, vol. 24 (8), pp. 1039-1049.
Office Action dated Jul. 19, 2011 for Japanese Application No. 2006526344, filed Sep. 10, 2004.
Opthalmed Inc., OMAC-260.
Pending Claims dated Jul. 29, 2009 for U.S. Appl. No. 11/618,411, filed Dec. 29, 2006.
Prosecution History for U.S. Appl. No. 10/958,871 (US20050234547), filed Oct. 5, 2004.
Prosecution History for U.S. Appl. No. 11/057,705 (US20060184244), filed Feb. 14, 2005.
Prosecution History for U.S. Appl. No. 11/195,422 (US20050267575), filed Aug. 1, 2005.
Prosecution History for U.S. Appl. No. 11/426,888, filed Jun. 27, 2006.
Ramocki J.M., et al., "Foldable Posterior Chamber Intraocular Lens Implantation in the Absence of Capsular and Zonular Support," American Journal of Ophthalmology, 1999, vol. 127 (2), pp. 213-216.
Simonov A.N., et al., "Cubic Optical Elements for an Accommodative Intraocular Lens," Optics Express, 2006, vol. 14 (17), pp. 7757-7775.
Storz Opthalmics Inc., Model L122UV ACL.
Supplementary European Search Report for Application No. EP00980998, dated Sep. 21, 2007, 2 pages.
Supplementary European Search Report for Application No. EP02748257, dated Jun. 13, 2008, 2 pages.
Supplementary European Search Report for Application No. EP03777934, dated Jan. 26, 2010, 3 pages.
Supplementary European Search Report for Application No. EP03809651, dated Aug. 11, 2006, 2 pages.
Supplementary European Search Report for Application No. EP04814069, dated Jul. 12, 2007, 1 page.
Taylor B.N., ed., The International System of Units (SI), 1991, NIST Special Publication 330, 4 pages.
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31 (11), pp. 2172-2179.
Universe IOL Center, Ocular Surgery News International.

* cited by examiner

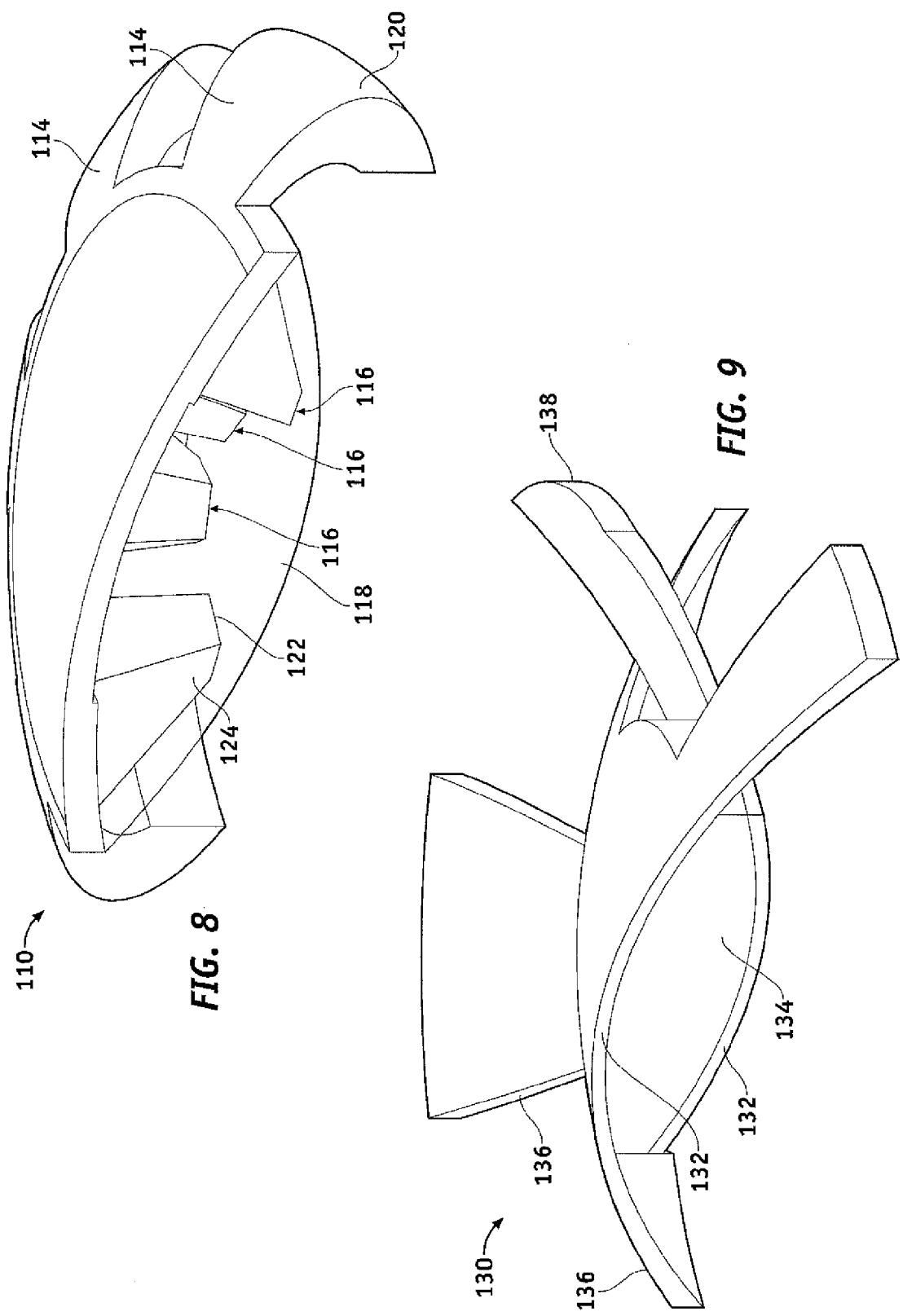

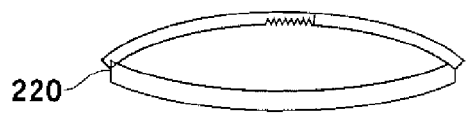
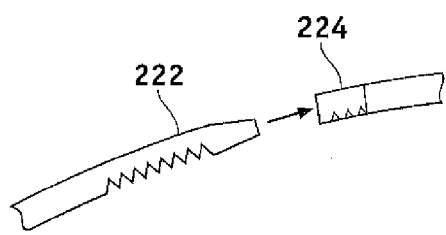
FIG. 14A
FIG. 14B
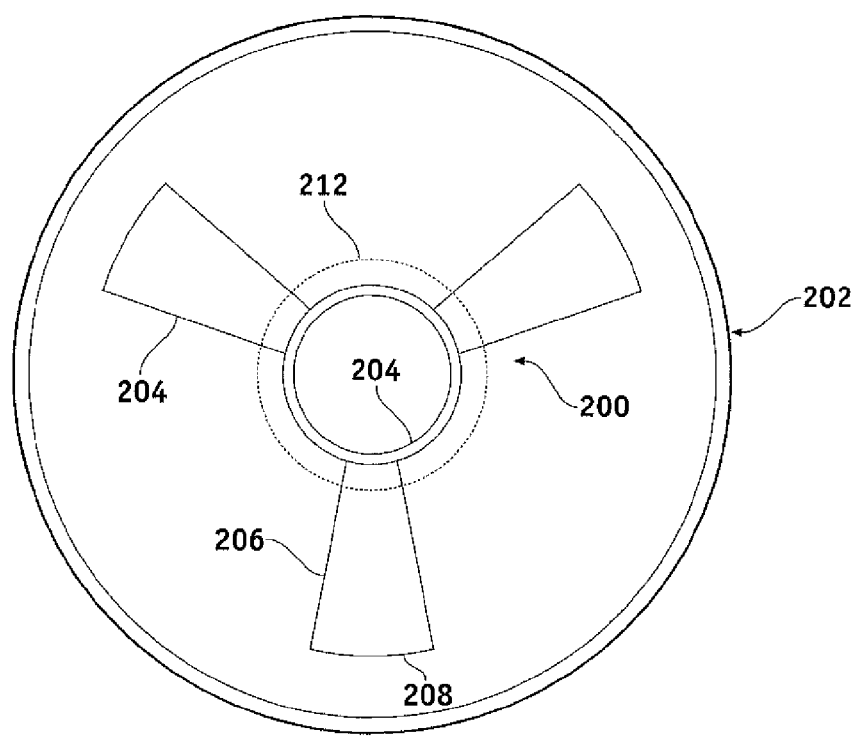
FIG. 13A
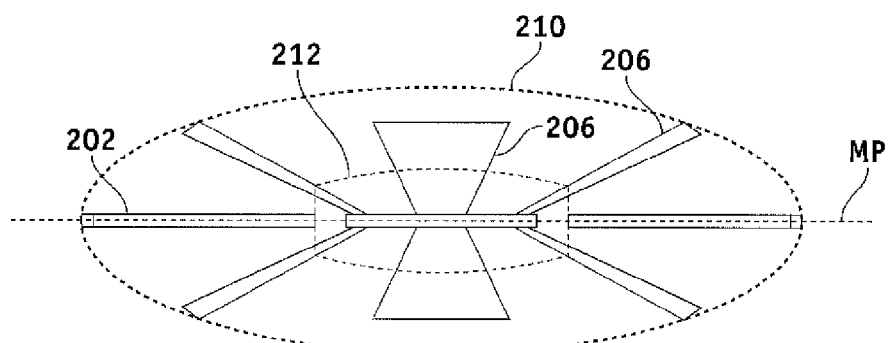
FIG. 13B

ACCOMMODATING INTRAOCULAR LENSES

The present application claims priority under 35 U.S.C. § 119(e) to provisional application No. 61/220,887, filed on Jun. 26, 2009 under the same title, which is incorporated herein by reference in its entirety. Full Paris Convention priority is hereby expressly reserved.

FIELD OF THE INVENTION

The present invention relates to intraocular lenses, and more particularly to accommodating intraocular lenses.

BACKGROUND OF THE INVENTION

A human eye can suffer diseases that impair a patient's vision. For instance, a cataract may increase the opacity of the lens, causing blindness. To restore the patient's vision, the diseased lens may be surgically removed and replaced with an artificial lens, known as an intraocular lens, or IOL. An IOL may also be used for presbyopic lens exchange.

The simplest IOLs have a single focal length, or, equivalently, a single power. Unlike the eye's natural lens, which can adjust its focal length within a particular range in a process known as accommodation, these single focal length IOLs cannot generally accommodate. As a result, objects at a particular position away from the eye appear in focus, while objects at an increasing distance away from that position appear increasingly blurred.

An improvement over the single focal length IOLs is an accommodating IOL, which can adjust its power within a particular range. As a result, the patient can clearly focus on objects in a range of distances away from the eye, rather than at a single distance. This ability to accommodate is of tremendous benefit for the patient, and more closely approximates the patient's natural vision than a single focal length IOL.

When the eye focuses on a relatively distant object, the lens power is at the low end of the accommodation range, which may be referred to as the "far" power. When the eye focuses on a relatively close object, the lens power is at the high end of the accommodation range, which may be referred to as the "near" power. The accommodation range or add power is defined as the near power minus the far power. In general, an accommodation range of 2 to 4 diopters is considered sufficient for most patients.

The human eye contains a structure known as the capsular bag, which surrounds the natural lens. The capsular bag is transparent, and serves to hold the lens. In the natural eye, accommodation is initiated in part by the ciliary muscle and a series of zonular fibers, also known as zonules. The zonules are located in a relatively thick band mostly around the equator of the lens, and impart a largely radial force to the capsular bag that can alter the shape and/or the location of the natural lens and thereby change its effective power.

In a typical surgery in which the natural lens is removed from the eye, the lens material is typically broken up and vacuumed out of the eye, but the capsular bag is left intact. The remaining capsular bag is extremely useful for an accommodating intraocular lens, in that the eye's natural accommodation is initiated at least in part by the zonules through the capsular bag. The capsular bag may be used to house an accommodating IOL, which in turn can change shape and/or shift in some manner to affect the power and/or the axial location of the image.

The IOL has an optic, which refracts light that passes through it and forms an image on the retina, and a haptic, which mechanically couples the optic to the capsular bag or holds the IOL in contact with the capsular bag. During accommodation, the zonules exert a force on the capsular bag, which in turn exerts a force on the optic. The force may be transmitted from the capsular bag directly to the optic, or from the capsular bag through the haptic to the optic.

One challenge in implementing an accommodating optic is designing a suitable haptic to couple the optic to the capsular bag. The haptic should allow distortion of the optic in an efficient manner, so that a relatively small ocular force from the ciliary muscle, zonules, and/or capsular bag can produce a relatively large change in power and/or axial location of the image. This reduces fatigue on the eye, which is highly desirable.

Accordingly, there exists a need for an intraocular lens having a haptic with increased efficiency in converting an ocular force to a change in power and/or a change in axial location of the image.

BRIEF DESCRIPTION OF THE DRAWINGS

Features and advantages of the present invention will become appreciated as the same become better understood with reference to the specification, claims, and appended drawings wherein:

FIG. 5A is a perspective view of a haptic for an intraocular lens having a central vaulted portion including spokes each having a unitary outer end and axially spaced apart bifurcated inner ends connected in two axially spaced planes;

FIG. 6A is a perspective view of a haptic similar to FIG. 5A but having a more conical central vaulted portion;

FIG. 6B is a perspective view of the haptic of FIG. 6A embedded within an accommodative optic;

FIG. 7 is a perspective view of a haptic similar to FIG. 5A embedded within an accommodative optic and having central throughholes in the vaulted portion;

FIG. 8 is a perspective view of an intraocular lens with a haptic having a central plate on one side of an optic midplane and a plurality of legs radiating outward therefrom, and including a circular array of teeth embedded in the optic;

FIG. 9 is a perspective view of an intraocular lens with a haptic having curved plate-like members that sandwich an optic therebetween, each curved plate-like member having a plurality of legs that extend outward therefrom;

FIG. 13A is a plan view of a system of a haptic for an intraocular lens and a posterior capsule opacification (PCO) ring, the haptic having a central ring from which a plurality of legs radiate outward at angles to the optic midplane;

FIG. 13B is an elevational view of the haptic of FIG. 13A positioned within a capsular bag shown in phantom;

FIGS. 14A and 14B are perspective and detailed views of an adjustable PCO ring.

DETAILED DESCRIPTION OF THE PREFERRED EMBODIMENTS

In a healthy human eye, the natural lens is housed in a structure known as the capsular bag. The capsular bag is driven by a ciliary muscle and zonular fibers (also known as zonules) in the eye, which can compress and/or pull on the capsular bag to change its shape. The motions of the capsular bag distort the natural lens in order to change its power and/or the location of the lens, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left intact in the eye, so that it may house the implanted intraocular lens.

Because the capsular bag is capable of motion, initiated by the ciliary muscle and/or zonules, it is desirable that the implanted intraocular lens change its power and/or location in the eye in a manner similar to that of the natural lens. Such an accommodating lens may produce improved vision over a lens with a fixed power and location that does not accommodate.

A desirable optic for an accommodating IOL is one that distorts in response to a squeezing or expanding radial force applied largely to the equator of the optic (i.e., by pushing or pulling on or near the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation. Furthermore, this method of changing the lens power reduces any undesirable pressures exerted on some of the structures in the eye.

Figure 1:
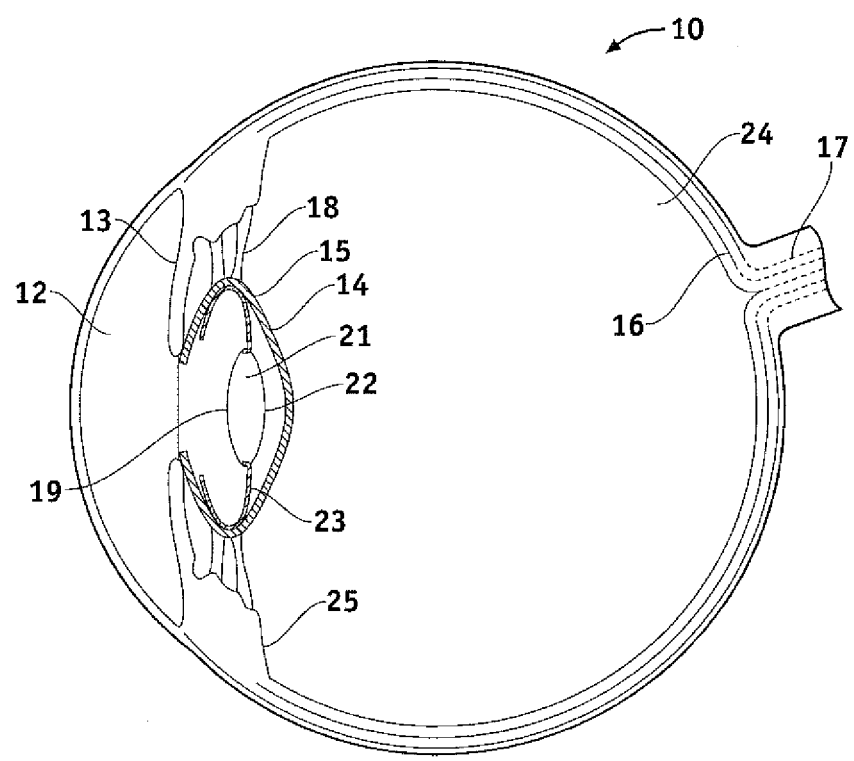
FIG. 1 is a plan drawing of a human eye having an implanted intraocular lens, in an accommodative or "near" state.

FIG. 1 shows a human eye 10, after an accommodating intraocular lens has been implanted. Light enters from the left of FIG. 1, and passes through the cornea 11, the anterior chamber 12, the iris 13, and enters the capsular bag 14. Prior to surgery, the natural lens occupies essentially the entire interior of the capsular bag 14. After surgery, the capsular bag 14 houses the intraocular lens, in addition to a fluid that occupies the remaining volume and equalizes the pressure in the eye. The intraocular lens is described in more detail below. After passing through the intraocular lens, light exits the posterior wall 15 of the capsular bag 14, passes through the posterior chamber 24, and strikes the retina 16, which detects the light and converts it to a signal transmitted through the optic nerve 17 to the brain.

A well-corrected eye forms an image at the retina 16. If the lens has too much or too little power, the image shifts axially along the optical axis away from the retina, toward or away from the lens. Note that the power required to focus on a close or near object is more than the power required to focus on a distant or far object. The difference between the "near" and "far" powers is known typically as the add power or as the range of accommodation. A normal range of accommodation is about 2 to 4 diopters, which is considered sufficient for most patients, but some have a range of 1 to 8 diopters.

The capsular bag is acted upon by the ciliary muscle 25 via the zonules 18, which distort the capsular bag 14 by stretching it radially in a relatively thick band about its equator. Experimentally, it is found that the ciliary muscle 25 and/or the zonules 18 typically exert a total ocular force of up to about 10 grams of force, which is distributed generally uniformly around the equator of the capsular bag 14. Although the range of ocular force may vary from patient to patient, it should be noted that for each patient, the range of accommodation is limited by the total ocular force that can be exert. Therefore, it is highly desirable that the intraocular lens be configured to vary its power over the full range of accommodation, in response to this limited range of ocular forces. In other words, it is desirable to have a relatively large change in power for a relatively small driving force.

Because the force exerted by the zonules, or ocular force, is limited, in some cases it is desirable to use a fairly thin lens, compared to the full thickness of the capsular bag. In general, a thin lens may distort more easily than a very thick one, and may therefore convert the ocular force more efficiently into a change in power. In other words, for a relatively thin lens, a lower force is required to cover the full range of accommodation. On the other hand, a soft, thicker lens may be capable of changing shape from small capsular bag forces and actually function better with fewer aberrations.

Note that the lens may be designed so that its relaxed state is the "far" condition (sometimes referred to as "disaccommodative biased"), the "near" condition ("accommodative biased"), or some condition in between the two.

The intraocular lens itself generally has two components, an optic 21, which is made of a transparent, deformable and/or elastic material, and a haptic 23, which holds the optic 21 in place and mechanically transfers forces on the capsular bag 14 to the optic 21. The haptic 23 may have an engagement member with a central recess that is sized to receive the peripheral edge of the optic 21. The haptic and optic may be refractive index matched, though if at least some of the haptic is embedded in or otherwise overlapping the optic the two materials must be index matched.

When the eye 10 focuses on a relatively close object, as shown in FIG. 1, the zonules 18 relax and compress the capsular bag 14 returns to its natural shape in which it is relatively thick at its center and has more steeply curved sides. As a result of this action, the power of the lens increases (i.e., one or both of the radii of curvature can decrease, and/or the lens can become thicker, and/or the lens may also move axially), placing the image of the relatively close object at the retina 16. Note that if the lens could not accommodate, the image of the relatively close object would be located behind the retina, and would appear blurred.

Figure 2:
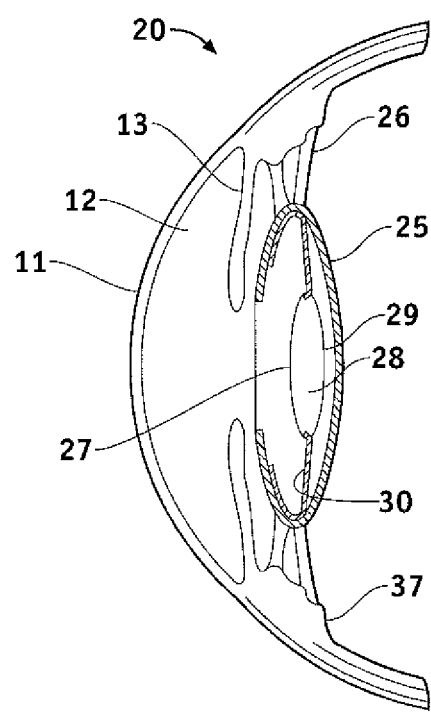
FIG. 2 is a plan drawing of the human eye of FIG. 1, in a disaccommodative or "far" state.

FIG. 2 shows a portion of an eye 20 that is focused on a relatively distant object. The cornea 11 and anterior chamber 12 are typically unaffected by accommodation, and are substantially identical to the corresponding elements in FIG. 1. To focus on the distant object, the ciliary muscle 37 contracts and the zonules 26 retract and change the shape of the capsular bag 25, which becomes thinner at its center and has less steeply curved sides. This reduces the lens power by flattening (i.e., lengthening radii of curvature and/or thinning) the lens, placing the image of the relatively distant object at the retina (not shown).

For both the "near" case of FIG. 1 and the "far" case of FIG. 2, the intraocular lens itself deforms and changes in response to the ciliary muscles and/or to the distortion of the capsular bag. For the "near" object, the haptic 23 compresses the optic 21 at its edge, increasing the thickness of the optic 21 at its center and more steeply curving its anterior face 19 and/or its posterior face 22. As a result, the lens power increases. For the "far" object, the haptic 30 expands, pulling on the optic 28 at its edge, and thereby decreasing the thickness of the optic 28 at its center and less steeply curving (e.g., lengthening one or both radius of curvature) its anterior face 27 and/or its posterior face 29. As a result, the lens power decreases.

Note that the specific degrees of change in curvature of the anterior and posterior faces depend on the nominal curvatures. Although the optics 21 and 28 are drawn as bi-convex, they may also be plano-convex, meniscus or other lens shapes. In all of these cases, the optic is compressed or expanded by forces applied by the haptic to the edge and/or faces of the optic. In addition, there may be some axial movement of the optic. In some embodiments, the haptic is configured to transfer the generally symmetric radial forces symmetrically to the optic to deform the optic in a spherically symmetric way. However, in alternate embodiments the haptic is configured non-uniformly (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optic may optionally have one or more diffractive elements, one or more multifocal elements, and/or one or more aspheric elements.

In many cases, it is desirable that during accommodation, the distortion of the optic produces a change in optic thickness and/or a change in the radius of curvature of the anterior and/or posterior surfaces of the optic. Any other types of distortions to the surface, such as "ripples" or "waves", may unacceptably degrade the optical performance of the lens. These "ripples" or "waves" are described in more detail below.

Because the optic is round, it may be difficult to envision any undesirable surface ripples that may accompany a squeezing or expanding of the optic about its equator. For this reason, it is instructive to consider the geometry of a linear beam or rod, which can produce analogous ripples along a single dimension. This 1-D geometry is much simpler to visualize, and adequately describes the issue of undesirable surface distortion.

Consider a linear beam or rod, which is being compressed by pushing on its ends. While the intended effect of the compression may be to shorten the beam and/or produce a slight bulge along the length of the beam, an unintended effect may be to cause a small amount of "buckling" along the length of the beam. Similarly, if the beam is stretched by pulling on its ends, the intended effect of the stretching may be to lengthen the beam and/or produce a slight thinning of the beam along its length, but an unintended effect may be to cause a small amount of "cracking" along the surface, similar in character to that of a desert floor. Both the "buckling" and "cracking" may occur along the surface of the beam, while the compression or expansion may be initiated at or near the ends of the beam.

This analogy may be extended to the two-dimensional, essentially circular geometry of the accommodating optic. To focus on relatively near objects, as in FIG. 1, the haptic may squeeze the optic about its equator and cause a radial compression of the optic. The intended effect of the squeezing may be to increase the thickness of the optic and/or change the curvature of the anterior and/or posterior surfaces of the optic. However, an unintended effect may be to produce the two-dimensional, circular equivalent of "buckling" on one or both of these surfaces. Similarly, to focus on relatively distant objects, as in FIG. 2, the haptic may stretch the optic about its equator and cause a radial expansion of the optic. The intended effect of the expansion may be to decrease the thickness of the optic and/or change the curvature of the anterior and/or posterior surfaces of the optic. However, an unintended effect may be to produce the twos dimensional, circular equivalent of "cracking" on one or both of these surfaces. For the purposes of this document, the circular equivalents of "buckling" and "cracking" may be referred to as "ripples" or "waves". For known optics, these "ripples" or "waves" may degrade the performance of the optic, which is highly undesirable.

It is possible that the "ripples" or "waves" during accommodation may be avoided if the optic has internal stress. For instance, if the haptic applies a compression or expansion force to the optic, separate and distinct from any compression or expansion forces applied by the capsular bag of the eye, then the optic may have some internal stress, which may reduce any "ripples" or "waves" that appear during accommodation. The internal stress in the optic may be present throughout the range of accommodation, or may alternatively pass through "zero" at some point in the range of accommodation.

In some embodiments, the anterior and/or posterior surfaces may be designed so that they attain particular profiles when the optic is compressed about its equator, as occurs when the lens is implanted. For instance, in some embodiments, it may be particularly desirable to have spherical anterior and/or posterior surfaces; in these embodiments, the anterior and/or posterior surface profiles may or may not deviate from spherical when the optic is uncompressed about its equator. In other words, for some embodiments, compressing the optic about its equator causes the anterior and/or posterior surfaces to become more spherical in profile. If there is a sphericity in either surface in the uncompressed state, it may be reduced when the optic is compressed.

For the purposes of this document, an intraocular lens and/or the optic contained therein in which a haptic uses its internal stress to affect the internal stress of the optic may be referred to as a "pre-stressed" intraocular lens and/or a "pre-stressed" optic.

Many embodiments herein provide a haptic partly embedded within an adjustable or accommodative central optic. The haptic transmits forces to alter at least one of the shape and the thickness of the adjustable optic. The materials of the haptic and optic may have similar compressive or spring moduli, to encourage direct transfer of forces and reduce uneven expansion/contraction and accompanying tension therebetween, though the haptics are generally somewhat stiffer to be capable of transmitting capsular forces. Additionally, similar material stiffness may reduce the mismatch in shrinkage rates during molding or post-processing, which mismatch may ultimately negatively impact lens resolution. In one embodiment, the stiffnesses of the two materials are within about 10% of each other and preferably within a range of about 20-100 kPa. Moreover, the two materials have similar refractive indices to reduce any unwanted glare or reflection from light passing across adjacent surfaces. A number of such embedded optics may be seen in U.S. Patent Publications 2008-0161913 and 2008-0161914, the disclosures of which are expressly incorporated herein.

A number of features described herein provide certain advantages to intraocular lenses. For instance, various configurations improve the accommodative performance of the haptic, such that compressive/tensile forces may be more efficiently transferred from the haptic to optic. Furthermore, certain aspects provide enhanced bag-sizing capability so that the IOL better fits within the capsular bag. Some of these features work together to provide both advantages, or may enhance the ability of another feature to perform its function. Indeed, it should be understood that any combination of individual haptic or IOL features described herein may be formed even if not explicitly described or shown.

Figure 3:
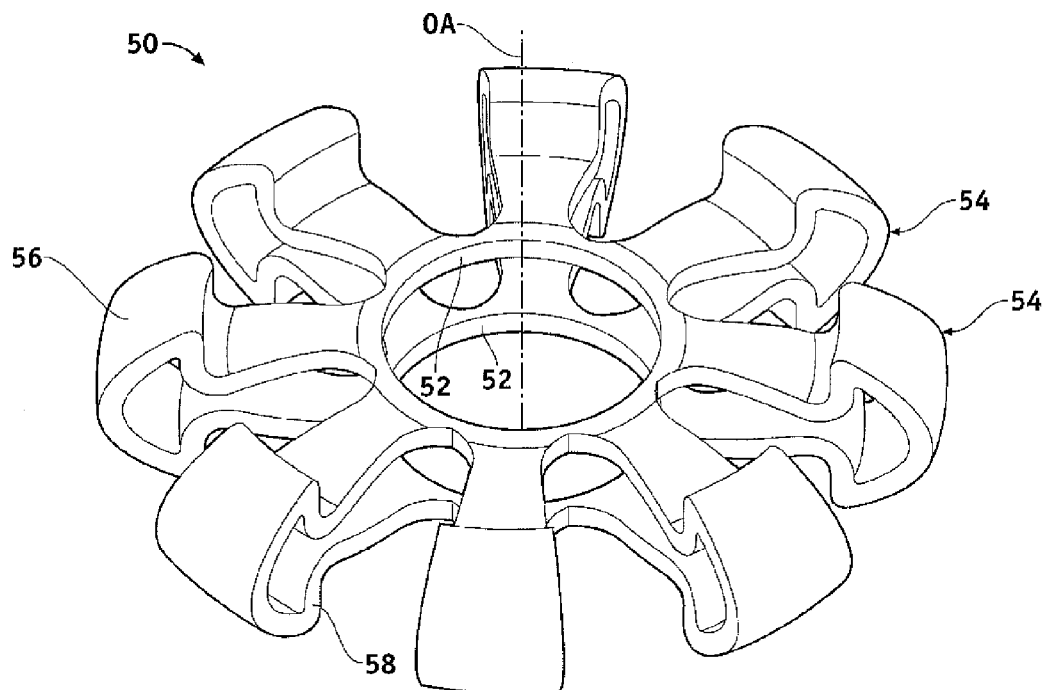
FIG. 3 is a perspective view of a haptic for an intraocular lens having a pair of axially spaced-apart and centered rings, and a plurality of plate-like legs radiating outward therefrom.

FIG. 3 is a perspective view of an accommodative haptic 50 for an intraocular lens having a pair of axially spaced-apart rings 52 centered around an optical axis OA, and a plurality of plate-like legs 54 radiating outward from each ring. The haptic 50 is desirably partly embedded within an adjustable or accommodative central optic (not shown) having an axial thickness through the center thereof. For instance, the haptic 50 may be embedded in the optic such that rings 52 are within the optic, but not all of the legs 54. The haptic 50 is configured to transmit forces to alter at least one of the shape and the thickness of the adjustable optic.

Desirably, the haptic 50 is symmetric across a midplane perpendicular to the optical axis OA such that there are matching legs 54 connected to each ring. Preferably, each pair of matching legs 54 joins together at their outer ends in a convex outer curve 56 that has an axial dimension greater than the spacing between the rings 52. That is, in the illustrated embodiment each two legs 54 and outer curve 56 are connected to form an arrowhead shape, with short concave sections 58 therebetween. As illustrated, there may be eight pairs of matching legs 54, though more and as few as three are contemplated. The arrowhead-shaped outer ends of the haptic legs 54 provides a capsular bag-filling outer profile to the haptic 50 that better couples the bag forces to the central softer optic to either expand or contract the optic axially. That is, forces exerted on the outer ends of the haptic legs 54 are transmitted through the legs to cause the spaced rings 52 to move apart or toward each other, thus changing the shape of the surrounding soft optic. The change in the surface shape of the optic changes the optic power thereof. Alternatively, it is also possible to provide two rigid optics, one attached to each of the two haptic rings 52, that move along the optical axis OA to create power change.

Figure 4:
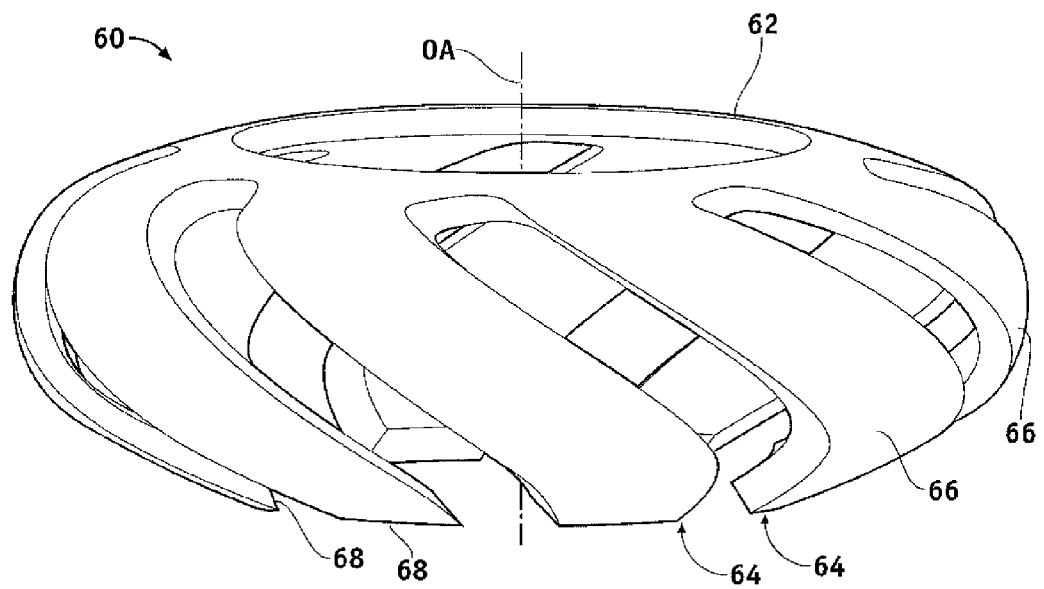
FIG. 4 is a perspective view of a haptic for an intraocular lens having a centered ring on one side of an optic midplane and a plurality of legs extending outward therefrom in similar spirals.

FIG. 4 is a perspective view of a further haptic 60 for an intraocular lens having a ring 62 centered around an optical axis OA and on one side of an optic midplane perpendicular to the axis. A plurality of legs 64 extend outward from the ring 62 in similar spirals and curve axially. The legs 64 define outermost convex curves 66 and continue radially inward on the opposite side of the optic midplane from the ring 62 to terminate in free ends 68. Indeed, the legs 64 are desirably outwardly convex along their lengths to conform closely to a surrounding capsular bag (not shown). The legs 64 preferably have a circumferential width that exceeds their radial thickness (as measured in the midplane). The resulting shape is analogous to a twisting pin-cushion.

As mentioned above, the haptic 60 is desirably partly embedded within an adjustable or accommodative central optic (not shown) having an axial thickness through the center thereof. For instance, the haptic 60 may be embedded in the optic such that ring 62 is within the optic, but not all of the legs 64. In one embodiment, the ring 62 and the free ends 68 of the legs are embedded in the optic, but the outermost convex curves 66 are not. The haptic 60 transmits forces imparted by the surrounding capsular bag to alter at least one of the shape and the thickness of the adjustable optic. As can be appreciated, a compressive force radially inward on the outermost convex curves 66 will tend to displace the ring 62 and the free ends 68 of the legs axially apart through the straightening or "unwinding" of the spiral legs 64.

The haptic 60 of FIG. 4 may incorporate two optics axially spaced along the optical axis OA such that at least one of the lenses rotates relative or opposite to the other during accommodation. For instance, one of the optics could be aspheric/asymmetrical such that the relative rotation causes a power change in addition to any power change caused by axial movement. In one embodiment, one optic spans and embeds the ring 62 and another optic spans and embeds the free ends 68. Although not shown here, it is also possible to construct a haptic that is similar to this one but symmetric about the horizontal plane so that two of the rings 62 are attached to the legs (without the free ends 68).

Figure 5B:
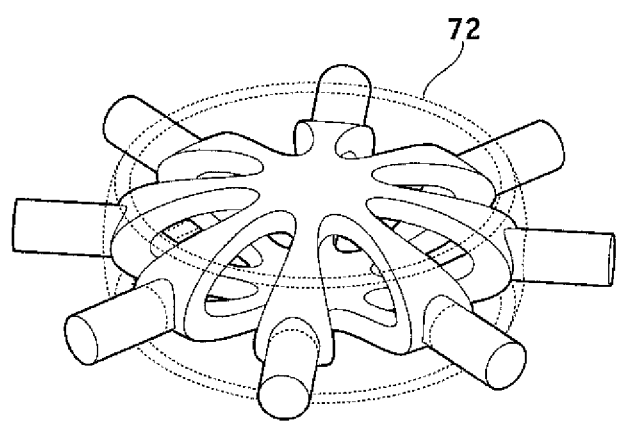
FIG. 5B is a perspective view of the haptic of FIG. 5A embedded within an accommodative optic.

FIG. 5A illustrates a haptic 70 for an intraocular lens, while FIG. 5B shows the haptic embedded within an accommodative optic 72 (shown translucent). The haptic 70 has a vaulted portion centered around an optical axis OA including spokes 74 each having a unitary outer end 76 and axially spaced apart bifurcated inner ends 78 connected in two axially spaced planes. In particular, the inner ends of the spokes 74 converge in two axially spaced-apart solid plates 80, denoted anterior and posterior plates. The vaulted spokes 74 resembles a cage structure. As mentioned above, the haptic 70 desirably is index matched with the optic 72.

The spokes 74 preferably have a circumferential width that exceeds their radial thickness (as measured in the midplane). More preferably, the circumferential width of the spokes 74 gradually increases from their connection with the central plates 80 outward to a maximum at their connection to the unitary outer ends 76. The term "unitary" is meant simply differentiate the bifurcated inner ends, and can be a variety of shapes. In the illustrated embodiment, the outer ends 76 comprises cylindrical rods or stubs that project radially outward from convex outer portions of the spokes 74. Rounded or other more bag-conforming structures may be provided on the outer ends of the cylindrical rods as desired.

As with the earlier haptics, the haptic 70 transmits forces imparted by the surrounding capsular bag to alter at least one of the shape and the thickness of the adjustable optic. Namely, a compressive force radially inward on the outer ends 76 will tend to spread the bifurcated inner spoke ends apart, thus separating the anterior and posterior plates 80 and accordingly axially thickening the optic 72. Conversely, a relaxation of the capsular bag forces causes the spokes 74 to return outward, thus allowing the anterior and posterior plates 80 to move together again. The radial length of the cylindrical rods 76 may be varied to provide a number of different sizes of IOLs so as to better fit various capsular bag sizes.

FIGS. 6A and 6B show a haptic 90 similar to that in FIG. 5A but having a more conical central vaulted portion 92. It is also worth mentioning that the haptics 70, 90 of FIGS. 5-6 include haptics having a central solid portion across the optical axis OA. By choosing materials of the haptic and optic that have similar refractive indices, the haptics can exist even across the central optic zone. This configuration makes possible a number of novel haptic shapes that may improve their accommodative performance. That is, compressive/tensile forces may be more efficiently transferred from the haptic to optic by providing this central solid zone.

FIG. 7 is a perspective view of a haptic 100 also similar to that in FIG. 5A embedded within an accommodative optic 102, yet having central throughholes 104 in the vaulted portion.

FIG. 8 shows another haptic 110 having a solid central plate 112 on one side of an optic midplane, and a plurality of legs 114 radiating outward therefrom. A circular array of teeth 116 projects generally axially (parallel to the optical axis) from one side of the central plate 112 and is embedded in a dome-like lens body 118. The central plate 112 is stiffer than the lens body 118, and the two are not necessarily index matched.

Each leg 114 has an outermost convex curve 120 to conform to the capsular bag. The curved outer ends of the haptic legs 114 provide a capsular bag-filling outer profile to the haptic 110 that better fits the interior of the bag. As with the other embodiments described herein, the legs 114 transmit forces exerted on the outer ends 120 to cause a change in surface shape or curvature of the lens body 118, thus changing the optic power.

Each tooth 116 defines a rectilinear solid that gradually narrows from a base at the central plate 112 to a tip 122. For instance, lateral sides 124 of each tooth 116 may have a modified quadrilateral shape as shown with an arcuate base at the central plate 112, two elongated linear sides and a short linear side at the tip 122. The teeth are angled generally normal to the concave inner surface of the plate 112 so that they converge radially inward toward each other. Desirably, the central plate 112, connected outer legs 114, and teeth 116 are all made of a stiffer material than the softer dome-like lens body 118. During accommodation, the teeth-like protrusions 116 of harder material inside the softer material of the body 118 act to further transmit the forces and alter the curvature of the lens body 118. The teeth 116 also act to squeeze the softer lens body 118 and cause its surface curvature to change, ideally in the opposite direction of the central plate 112, to enhance power change.

FIG. 9 illustrates a further haptic 130 having opposed curved plate-like members 132 that sandwich an optic 134 therebetween. Each plate-like member 132 defines a concave face toward the optic 134 and a convex face away from the optic, and a plurality of legs 136 that extend outward from the perimeter of the optic along generally the same curvature to contact the capsular bag (however, in some cases dissimilar haptic leg curvatures may be desirable). The haptic legs 136 of the opposed plate-like members 132 are interwoven so as to present alternating axially-spaced legs to support the inside of the capsular bag. Moreover, the legs 136 are desirably wider than they are thick, so as to form curved plates, and have a width that increases radially outward to resemble the legs of an Iron Cross. The outer edges 138 of the legs 136 are the widest, and are desirably angled or contoured to more closely match the curvature of the surrounding capsular bag. Other conforming structure may be used, such as the flexible tips described below.

The opposing plate-like members 132 including the outer legs 136 are typically stiffer materials than the softer optic 134. As before, the haptic 130 transmits forces from the surrounding capsular bag to alter at least one of the shape and the thickness of the adjustable optic 134. The stresses transmitted through the outer legs 136 causes the plate-like members 132 to bow or flatten, which then alters the thickness and/or curvature of the softer central optic 134. As with most of the configurations described herein, the different materials would typically be refractive index matched to avoid unwanted optical effects. In some configurations, some difference in refractive index is acceptable.

Figure 10:
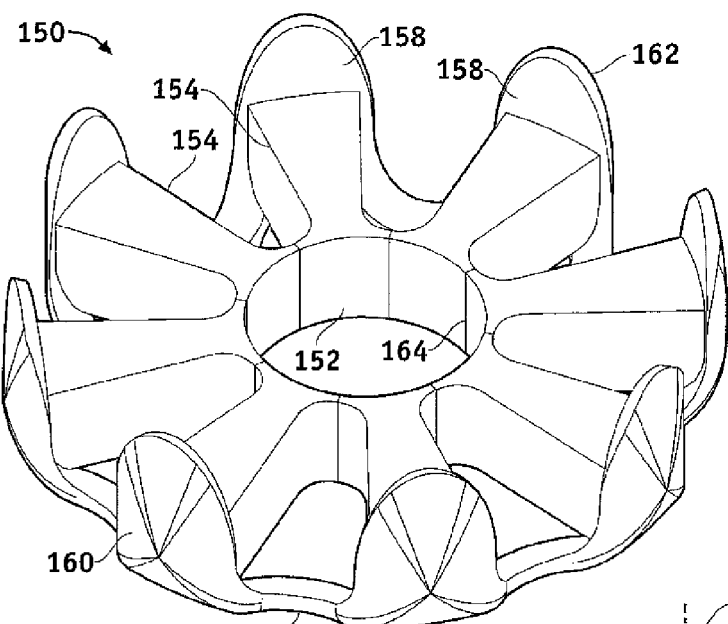
FIG. 10 is a perspective view of a haptic for an intraocular lens having a centered ring and a plurality of legs radiating outward each having an outer end capped with a flap-like appendage for fitting within a capsular bag.

The haptic 150 of FIG. 10 includes a centered ring 152 and a plurality of spoke-like legs 154 radiating outward therefrom. Each leg 154 has an outer end connected by a peripheral ring 156 and is capped with a flap-like appendage 158 for fitting within a capsular bag. More specifically, the flap-like appendage 158 extends generally axially in at least one direction from the outer end of the respective leg 154. To better conform to the capsular bag, each appendage 158 features a rounded or convex outer surface 160 and an arcuate free edge 162 at its axial extent.

As before, the haptic 150 is configured to transmit forces from the capsular bag to alter at least one of the shape and the thickness of an adjustable optic (not shown) within which the haptic is embedded. The legs 154 are wedge-shaped with narrower inner ends at the centered ring 152 and wider outer ends at the peripheral ring 156. FIG. 10 also shows optional cuts 164 in the inner ring 152 that assist in reducing the resistance of movement of the ring to radial pressure from the bag. The cuts 164 may also be wider spaces or slots.

The flap-like appendages 158 provide some flexibility or resilience at the outer ends of the legs 154 so that the sizing of the intraocular lens within the capsular bag is not as critical. That is, the capsular bag is measured and an IOL chosen therefrom, but due to an incremental size selection of haptics the spectrum of capsular bag sizes cannot be precisely matched. However, the appendages 158 are cantilevered from the legs 154 so that they bend somewhat if the bag is slightly smaller than expected, thus providing a better structural engagement with the bag. The haptic 150 is thus bag-size forgiving in that the floppy appendages 158 will give more or less depending on bag size. Further, the appendages 158 store some potential energy from bending to help assist in transmitting bag forces into the central optic.

Figure 11:
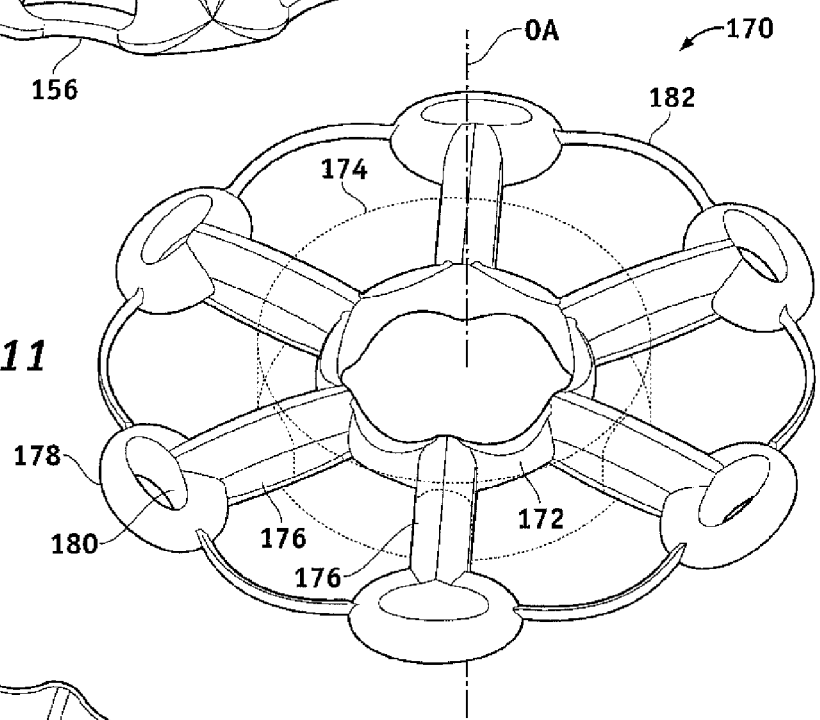
FIG. 11 is a perspective view of a haptic for an intraocular lens having a centered ring and a plurality of legs radiating outward each leg having an outer end that terminates in an annular tip.

FIG. 11 shows another haptic 170 for an intraocular lens having a centered ring 172 embedded in an optic 174 and a plurality of legs 176 radiating outward therefrom. Each leg 176 terminates in an outer end that defines an annular tip 178. Each annular tip 178 is oriented generally parallel to the centered ring 172 such that an oval-shaped central opening 180 therein has an axis parallel to the optical axis OA. The annular tips 178 are connected by a peripheral ring 182 with bowed out sections between the legs 176.

The haptic legs 176 act as bumpers to allow some forgiveness in bag-sizing whereby the annular tips 178 flex and absorb compressive forces from the surrounding capsular bag. The bowed out sections of the peripheral ring 182 also assist this flexing. This enhances the ability of the haptic 170 to be properly sized within a range of bag sizes and shapes. The peripheral ring 182 helps even out capsular bag forces to adjacent legs 176. The tips 178 and bowed out sections of the peripheral ring 182 give or squeeze a bit without compromising the accommodating function of the IOL. Preferably there is some give which does not significantly affect the magnitude of force from the bag being applied into the central optic, or responsiveness to such capsular bag movement.

It should also be noted that all surfaces of the haptic 170 are rounded to enhance conformity to the capsular bag and reduce irritation that might occur from abrasion of sharp corners. The rounded surfaces also help to reduce glare and reflections.

Figure 12A:
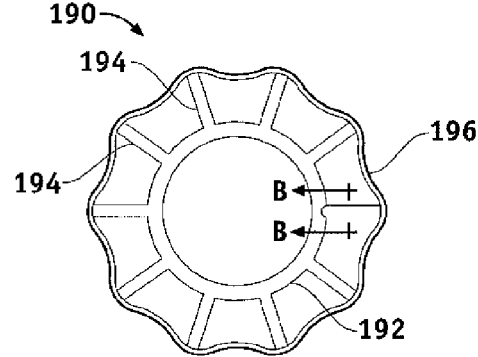
FIGS. 12A and 12B are plan and detailed sectional views of a haptic for an intraocular lens having a centered ring and a plurality of legs radiating outward therefrom, each leg having a rounded cross-section.
Figure 12B:
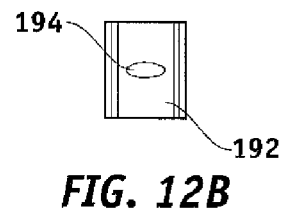

FIG. 12A is a plan view of a further haptic 190 for an intraocular lens having a centered ring 192, a plurality of legs 194 radiating outward therefrom, and a peripheral ring 196 connecting the outer ends of the legs. As seen in the detail of FIG. 12B, each leg has a rounded cross-section as with the haptic 170 above to reduce irritation with the capsular bag, as well as optical glare and reflections. The peripheral ring 196 has an undulating circumferential profile with inward bows between the legs 194.

FIGS. 13A and 13B illustrate a system of a haptic 200 for an intraocular lens and a surrounding posterior capsule opacification (PCO) ring 202. The haptic 200 has a circular ring 204 in the optic midplane MP from which a plurality of legs 206 radiate outward at angles to the optic midplane to form two circumferential and axially-spaced arrays of haptic leg ends 208 to contact a capsular bag 210, shown in phantom in FIG. 13B. The haptic 200 is partly embedded within an adjustable optic 212 and provides accommodation thereto as described. There are preferably at least three haptic legs 206 angled to each side of the optic midplane MP as shown, though more may be utilized (for instance, an Iron Cross configuration as above). The legs 206 may be arranged symmetrically across the optic midplane MP as shown or offset circumferentially. The anterior and posterior side legs 206 are desirably equivalent in size and shape, though different lengths and/or configurations are contemplated. Likewise, the number of legs 206 on each side of the optic midplane MP may not be equal.

The two-piece IOL system including the haptic 200 and PCO ring 202 may be implanted separately, typically the ring 202 first. The PCO ring 202 is formed as thin as possible and will not affect accommodation provided by the haptic 200 to the optic 202. The system accomplishes bag-sizing and PCO prevention by using the capsular tension-type ring 202 around the bag equator to limit the migration of lens epithelial cells (i.e. PCO) from the equator behind the optic 212. The haptic legs 206 are offset angularly so that they do not terminate along the equator and interfere with the PCO ring. Some non-contiguous IOL designs may allow PCO to creep in behind the optic, and therefore PCO is handled by including the solid ring 202, preferably with a sharp edge, with the haptic 200 shaped to work around that ring.

FIGS. 14A and 14B are perspective and detailed views of an adjustable PCO ring 220 that may be used in place of the solid ring 202 of FIGS. 13A-13B. The ring 220 may include, for example, a zip-tie configuration with a male end 222 having ratchet teeth that fits into a female end 224 with a mating sleeve or pocket. The adjustable PCO ring 220 is used to both adjustably size itself against the capsular bag and also provide a measurement of the bag size based on the amount that the ring is contracted to fit. This can be calibrated to the number of teeth clicks, for example. The zip-tie ring will really help address (IOL) sizing in vivo and help ensure contact with the periphery of capsular bag to translate forces from ciliary body/zonules for accommodation while preventing PCO.

It should be noted that the rings 202, 220 in FIG. 13 or 14 could also provide a drug-delivery type system, such as a drug-eluting material, to further help prevent PCO.

Figure 15A:
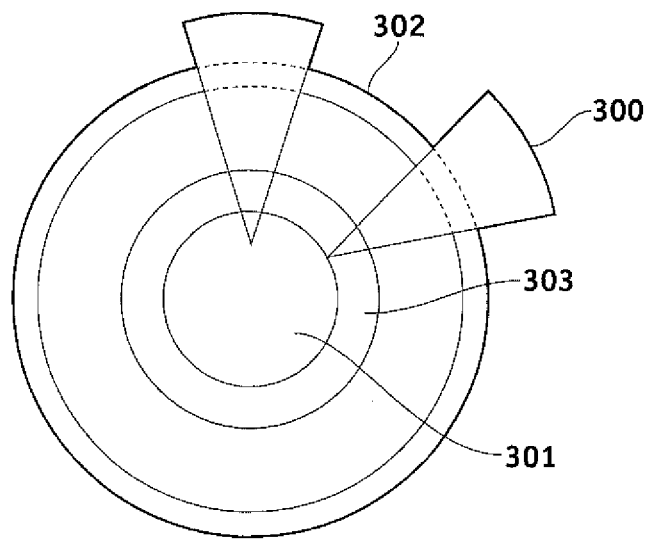
FIGS. 15A and 15B illustrate an intraocular lens having a centered ring, a plurality of haptics radiating outward therefrom, each haptic having an outer end that terminates in an annular tip lying generally parallel to the centered ring, and an inflatable outer ring.
Figure 15B:
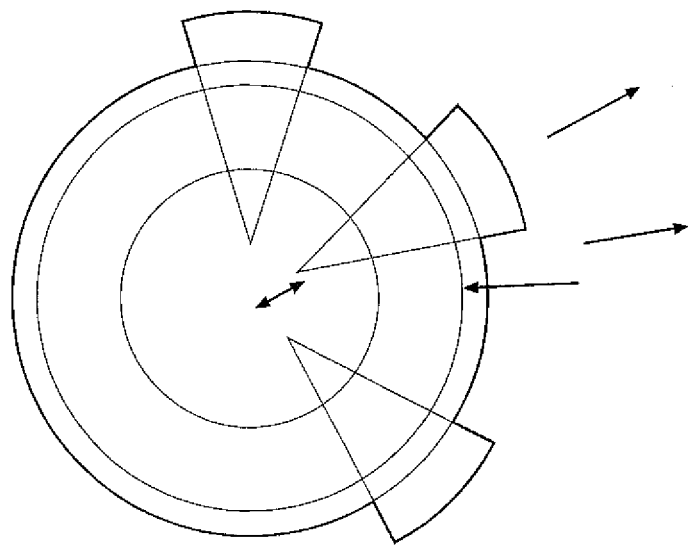

According to another embodiment, an IOL may comprise one or more haptics and/or one or more rings around an optic, wherein the haptics and/or rings may be inflated. Inflation of the haptics and/or rings may adjust the size of the haptics and/or rings to create a better fit within the capsular bag and/or alter the stress on the optics. The haptics may be of varying shapes, including but not limited to a pie or wedge shape as illustrated in FIGS. 15A and 15B, a wheel/spoke configuration, or other configuration described herein. The level of inflation of the haptics and/or rings may be adjusted at the time of the initial implantation of the IOL. The level of inflation may also be adjusted or fine tuned during the life of the IOL, including but not limited to soon after implantation, and/or months or years after implantation. The fine tuning or adjustment may be made to enhance the patient's visual outcome over time. The haptics may be filled with anything known in the art including, but not limited to, saline, air, and/or silicone. The optic, haptics, and/or rings may have varying flexibility/stiffness depending upon the needs of the patient, the characteristics of the patient's eye, and/or the desired characteristics of the IOL. The haptics and/or rings may also have multiple chambers within each haptic and/or ring that are inflatable. Each chamber may be filled to different levels, thereby customizing the shape of the IOL to the capsular bag and/or varying the stresses on the optic to allow for non-uniform transfer of forces by the haptic to the optic.

FIGS. 15A and 15B illustrate an embodiment of the present invention. In FIG. 15A, multiple wedge shaped haptics are shown radiating outward around a center optic. The haptics are connected to an inner ring of the optic and an inflatable outer ring. Inflation of the outer ring adjusts the overall size of the IOL, as seen in FIG. 15B, enabling better fit of the IOL within the capsular bag. The inflation may also place stress on the optics as the haptics are connected to the inner ring of the optic and the inflatable outer ring. Such stress may change the thickness and/or shape of the optic. It is also envisioned that an IOL of the present invention comprises an inflatable inner ring and an inflatable outer ring, both of which are adjustable. The inner ring may be connected to the optic.

While the invention has been described in its preferred embodiments, it is to be understood that the words which have been used are words of description and not of limitation. Therefore, changes may be made within the appended claims without departing from the true scope of the invention.

What is claimed is:

1. An intraocular lens for implantation into an eye, comprising:
    a deformable optic having an anterior face, a posterior face, and an axial thickness through a center thereof; and
    a haptic comprising a vaulted portion centered around an optical axis and a plurality of spokes, each spoke comprising a pair of spoke segments including a first spoke segment and a second spoke segment, wherein each pair of spoke segments extends between a respective unitary outer end and respective inner ends bifurcated in a direction along the optical axis, wherein, for each respective pair of spoke segments, the first spoke segment of the respective pair is spaced apart in the direction along the optical axis from the second spoke segment of the respective pair by a respective gap, the respective gap extending radially from the respective bifurcated inner ends to the respective unitary outer end of the respective pair of spoke segments, wherein the first spoke segment and the second spoke segment of each pair of spoke segments are entirely embedded within the deformable optic, wherein the spokes lie in a plane perpendicular to the optical axis, and whereby the haptic is configured to transmit forces that result in the bifurcated inner ends of each pair of spoke segments vaulting to increase the respective gap between the first and second spoke segments of each pair of spoke segments and to increase the axial thickness of the deformable optic thereby more steeply curving the anterior face and the posterior face such that the anterior face and posterior face move apart from each other to change an accommodation of the intraocular lens.

2. The intraocular lens of claim of claim 1, wherein the haptic further comprises a first central plate and a second central plate spaced apart from the first central plate along the optical axis, the first central plate connecting innermost ends of the first spoke segments of each pair of spoke segments, the second central plate connecting innermost ends of the second spoke segments of each pair of spoke segments.

3. The intraocular lens of claim 2, wherein the spokes have a circumferential width that exceeds a radial thickness of the spokes.

4. The intraocular lens of claim 3, wherein the circumferential width of the spokes gradually increases from their connection with the first and second central plates outward to a maximum at their connection to the respective unitary outer ends.

5. The intraocular lens of claim 1, wherein the haptic further comprises cylindrical rods or stubs that project radially outward from the respective unitary outer ends of the spokes.

6. The intraocular lens of claim 1, wherein the respective unitary outer ends of the spokes are rounded.

7. The intraocular lens of claim 1, wherein the central vaulted portion is conical.

8. The intraocular lens of claim of claim 7, wherein the bifurcated inner ends of the spokes are connected in two axially spaced planes.

9. The intraocular lens of claim 7, wherein the spokes have a circumferential width that exceeds their radial thickness.

10. The intraocular lens of claim 9, wherein the circumferential width of the spokes gradually increases from their connection with central plates outward to a maximum at their connection to the respective unitary outer ends.

11. The intraocular lens of claim 7, wherein each unitary outer end is comprised of a cylindrical rod or stub that projects radially outward from respective outer portions of the spokes.

12. The intraocular lens of claim 7, wherein each unitary outer end is rounded.

13. The intraocular lens of claim 1, wherein the central vaulted portion is comprised of central throughholes.

14. The intraocular lens of claim of claim 13, wherein the bifurcated inner ends of the spokes are connected in two axially spaced planes.

15. The intraocular lens of claim 13, wherein the spokes have a circumferential width that exceeds their radial thickness.

16. The intraocular lens of claim 15, wherein the circumferential width of the spokes gradually increases from their connection with central plates outward to a maximum at their connection to the respective unitary outer ends.

17. The intraocular lens of claim 13, wherein each unitary outer end is comprised of a cylindrical rod or stub that projects radially outward from respective outer portions of the spokes.

18. The intraocular lens of claim 13, wherein each unitary outer end is rounded.

* * * * *